(12) United States Patent
Ackeret et al.

(10) Patent No.: US 6,379,360 B1
(45) Date of Patent: Apr. 30, 2002

(54) SPIRAL BLADE INSERTION INSTRUMENT

(75) Inventors: Roman Ackeret, Rheinfelden; Peter Senn, Waldenburg; Ruth Hungerbühler, Langenbruck, all of (CH)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/658,386

(22) Filed: Sep. 8, 2000

Related U.S. Application Data

(63) Continuation of application No. PCT/CH99/00074, filed on Feb. 16, 1999.

(30) Foreign Application Priority Data

Mar. 11, 1998 (DE) ..................................... 298 04 268 U

(51) Int. Cl.[7] .............................................. A61B 17/72
(52) U.S. Cl. ......................................... 606/67; 606/60
(58) Field of Search ............................ 606/60, 62, 64, 606/67, 86, 96, 98

(56) References Cited

U.S. PATENT DOCUMENTS

| | | | |
|---|---|---|---|
| 3,596,656 A | 8/1971 | Kaute | 128/92 |
| 4,080,666 A | 3/1978 | Fixel | 3/1.91 |
| 4,103,683 A | 8/1978 | Neufeld | 128/92 BA |
| 4,172,452 A | 10/1979 | Forte et al. | 128/92 BA |
| 4,232,985 A * | 11/1980 | Nielsen | 408/226 |
| 4,438,762 A | 3/1984 | Kyle | 128/92 BB |
| 4,441,492 A | 4/1984 | Rydell et al. | 128/92 EB |
| 4,494,535 A | 1/1985 | Haig | 128/92 BA |
| 4,567,001 A | 1/1986 | VanRheenen | 260/397.3 |
| 4,612,920 A | 9/1986 | Lower | 128/92 BA |
| 4,621,628 A | 11/1986 | Brudermann | 128/92 VD |
| 4,622,959 A * | 11/1986 | Marcus | 606/64 |
| 4,657,001 A | 4/1987 | Fixel | 128/92 YS |
| 4,697,585 A | 10/1987 | Williams | 128/92 YZ |
| 4,733,654 A | 3/1988 | Marino | 128/92 YY |
| 4,776,330 A | 10/1988 | Chapman et al. | 128/92 YY |
| 4,791,918 A | 12/1988 | Von Hasselbach | 128/924 K |
| 4,823,780 A * | 4/1989 | Odensten et al. | 606/96 |
| 4,827,917 A | 5/1989 | Brumfield | 128/42 YZ |

(List continued on next page.)

FOREIGN PATENT DOCUMENTS

| | | |
|---|---|---|
| EP | 0 586 824 A1 | 3/1994 |
| EP | 0 551 588 B1 | 3/1997 |
| EP | 0 853 923 A1 | 7/1998 |
| EP | 0 922 437 A1 | 6/1999 |
| GB | 2 209 947 A | 6/1989 |
| JP | 09-066059 | 3/1997 |
| JP | 09-066060 | 3/1997 |
| JP | 09-066061 | 3/1997 |
| JP | 09-220235 | 8/1997 |
| JP | 10-221630 | 8/1998 |
| JP | 11-137566 | 5/1999 |
| WO | WO 98/05263 | 2/1998 |
| WO | WO 99/20195 | 4/1999 |
| WO | WO 99/44528 | 9/1999 |

Primary Examiner—Jeffrey A. Smith
Assistant Examiner—Michael B. Priddy
(74) Attorney, Agent, or Firm—Pennie & Edmonds LLP

(57) ABSTRACT

The invention relates to a device for introducing a spiral blade into an intramedullary nail. The device includes a target-finding stay with a through hole, a guide sleeve attached coaxially in relation to the through hole, and a mandrel which is able to slide in the guide sleeve. The spiral blade is removable attached to the front end of the mandrel. The peripheral surfaces of the mandrel and the through hole of the guide sleeve have engaging mechanisms that interact with each other in such a way that the mandrel can be moved in the through hole of the guide sleeve only in a screw-like manner. An axially movable tissue-protective sleeve can be attached coaxially in relation to the mandrel.

20 Claims, 5 Drawing Sheets

U.S. PATENT DOCUMENTS

| | | | | |
|---|---|---|---|---|
| 4,858,602 A | | 8/1989 | Seidel et al. | 128/92 YY |
| 4,973,332 A | | 11/1990 | Kummer | 606/65 |
| 4,978,349 A | | 12/1990 | Frigg | 606/67 |
| 5,032,125 A | | 7/1991 | Durham et al. | 606/62 |
| 5,041,114 A | | 8/1991 | Chapman et al. | 606/62 |
| 5,047,034 A | * | 9/1991 | Sohngen | 606/87 |
| 5,112,333 A | | 5/1992 | Fixel | 606/62 |
| 5,116,336 A | | 5/1992 | Frigg | 606/65 |
| 5,167,663 A | | 12/1992 | Brumfield | 606/64 |
| 5,176,681 A | * | 1/1993 | Lawes et al. | 606/64 |
| 5,300,074 A | | 4/1994 | Frigg | 128/67 |
| 5,312,406 A | | 5/1994 | Brumfield | 606/64 |
| 5,312,409 A | * | 5/1994 | McLaughlin et al. | 606/86 |
| 5,342,363 A | * | 8/1994 | Richelsoph | 606/79 |
| 5,352,228 A | * | 10/1994 | Kummer et al. | 606/64 |
| 5,454,813 A | | 10/1995 | Lawes | 606/62 |
| 5,484,439 A | | 1/1996 | Olson et al. | 606/65 |
| 5,562,666 A | | 10/1996 | Brumfield | 606/64 |
| 5,578,035 A | | 11/1996 | Lin | 606/68 |
| 5,591,168 A | | 1/1997 | Judet et al. | 606/65 |
| 5,613,971 A | * | 3/1997 | Lower et al. | 606/96 |
| 5,620,449 A | * | 4/1997 | Faccioli et al. | 606/98 |
| 5,658,339 A | | 8/1997 | Tronzo et al. | 623/18 |
| 5,713,902 A | | 2/1998 | Friedl | 606/64 |
| 5,728,099 A | | 3/1998 | Tellman et al. | 606/65 |
| 5,741,256 A | | 4/1998 | Bresina | 606/62 |
| 5,749,872 A | | 5/1998 | Kyle et al. | 606/69 |
| 5,888,206 A | | 3/1999 | Lob et al. | 623/23 |
| 5,908,422 A | | 6/1999 | Bresina | 606/67 |
| 5,928,235 A | | 7/1999 | Friedl | 606/64 |
| 6,039,739 A | * | 3/2000 | Simon | 606/64 |

* cited by examiner

SPIRAL BLADE INSERTION INSTRUMENT

CROSS-REFERENCE TO RELATED APPLICATIONS

This application is a continuation of the U.S. National Stage designation of co-pending International Patent Application PCT/CH99/00074, filed Feb. 16, 1999, which claims priority to German Application No. 298 04 268.1, filed Mar. 11, 1998. The entire content of both of these applications is expressly incorporated herein by reference thereto.

FIELD OF THE INVENTION

The present invention relates to a device for introducing a spiral blade into an intramedullary nail.

BACKGROUND OF THE INVENTION

Intramedullary nails are frequently used for internal fixation of long bones such as the femur. These intramedullary nails are often used in conjunction with a locking element for securing the intramedullary nail within the medullary canal. One such locking element is a spiral blade. The intramedullary nail has a borehole for receiving the spiral blade. Because of the spiral blade geometry, the borehole has an elongated cross-section, for instance in the form of a slot or in a keyed opening of similar shape. As the borehole for the spiral blade in the intramedullary nail is only slightly larger than the spiral blade, the spiral blade can be inserted into the nail only at certain rotational angles. As the spiral blade is inserted through the borehole, the spiral blade must rotate about its longitudinal axis to avoid excessive removal of bone. However, in order to align the spiral blade with the elongated borehole in the nail, the spiral blade must be in a specific position when it enters the nail.

With prior art devices for insertion of a spiral blade, a hole would be drilled through the bone until the intramedullary nail is reached so that the proper orientation of the spiral blade could be determined. In so doing, significant bone must be removed. This loss of bone can compromise the stability of the spiral blade when it is inserted.

Thus, there exists a need for an improved spiral blade insertion instrument.

SUMMARY OF THE INVENTION

The present invention relates to an insertion instrument for inserting a spiral blade through a borehole in an implanted intramedullary nail. The instrument includes a targeting strap having first and second arms, a guide sleeve operatively associated with the targeting strap and having a first engaging element, and a mandrel having a second engaging element. The first arm of the targeting strap has a through hole, while the guide sleeve has an opening running coaxially with the through hole. The mandrel is slideably receivable in the opening. The first and second engaging elements cooperate to convert an axial force on the mandrel to helical motion of the mandrel such that a spiral blade detachably mounted to the distal end of the mandrel is properly oriented to be received by the borehole.

In order to position and secure the targeting strap to the intramedullary nail, a targeting strap tube insertable in a hole in the second arm receives a connecting member. The first and second engaging elements are positioned with respect to each other so that the mandrel intersects an axis of the targeting strap tube. This axis intersects a central axis of the guide sleeve and runs at an angle thereto.

The proximal end of the mandrel can have a head that has a diameter larger than that of the opening so that the head contacts a proximal end of the guide sleeve when the spiral blade is received in the borehole. The insertion device can also include a limiting element securable on the mandrel for limiting the amount of movement of the mandrel into the opening. In order to provide adjustability, the limiting element is securable on the mandrel in any one of a plurality of positions.

In one embodiment, the first engaging element is a pin extending across the central axis of the guide sleeve and the second engaging element is a spiral groove on the mandrel. The pin engages the spiral groove to allow helical motion of the mandrel. The second engaging element can comprise first and second spiral grooves mutually offset by about 180 degrees on a lateral surface of the mandrel. The first and second spiral grooves pitch can match the pitch of the spiral blade. The first engaging element can include first and second pins extending across the central axis of the guide sleeve and configured and dimensioned so that each of the first and second pins engages one of the first and second spiral grooves.

In another embodiment, the first engaging element is a thread on a lateral surface of the mandrel and the second engaging element is a mating thread on the opening in the guide sleeve.

The insertion instrument can also include a tissue protective sleeve with the guide sleeve attached to the first arm of the targeting strap. The tissue protective sleeve has a bore running coaxially with the central axis. At least a portion of the tissue protective sleeve is slidably received in the opening of the guide sleeve. The tissue protective sleeve can have a handle and the guide sleeve can have a slot. The handle is moveable within the slot to slide the tissue protective sleeve in the opening of the guide sleeve and prevent rotation of the tissue protective sleeve. A lateral surface of the tissue protective sleeve can be provided with indicia for selectable axial positioning. In one embodiment, the mandrel has a shoulder that contacts a proximal end of the tissue protective sleeve when the spiral blade is received in the borehole.

The present invention also relates to an insertion instrument for inserting a spiral blade through a borehole in an implanted intramedullary nail. The instrument comprises a targeting strap having first and second arms and a through hole in the first arm, an alignment element associated with the through hole, and a spiral blade that cooperates with the alignment element to align the blade with the borehole in the nail. In one embodiment, the alignment element comprises a pin.

With the insertion instrument of the present invention, the distance between the intramedullary nail and the end of the spiral blade at the beginning of the guided movement is always the same due to the design of the targeting strap. The spiral blade is positioned so that when it is inserted into the intramedullary nail, the spiral blade has a rotational orientation that corresponds with the geometry of the elongated borehole. This alignment of the spiral blade with the borehole is achieved independently of the width of the condyle, and independently of the entry point of the spiral blade into the bone.

Furthermore, the insertion instrument of the present invention makes it possible for the mandrel to be driven against the bone only so far that the mandrel reaches the bone when the spiral blade is introduced. This precise positioning of the spiral blade in the bone can be accomplished in the following ways:

by eye, without any visual assistance;

by radiology;

by using a monitor and cameras that can be brought close to the bone;

by measuring the distance between the device and the bone and securing a locking ring on the mandrel to function as a stop;

by bringing the mandrel to the bone before installing the spiral blade and at the same time securing a locking ring on the mandrel to function as a stop;

by means of a calibrated tissue protection sleeve around the mandrel which makes the device axially displaceable (the dimension reading on the calibrated tissue protection sleeve is set with the help of a stop on the mandrel which is stopped by the guide sleeve when the spiral blade is received in the borehole, thereby correctly positioning the spiral blade in the axial direction);

by configuring the mandrel to have a larger diameter than the spiral blade and is in contact with the bone when the spiral blade is received by the borehole; and by designing the tissue protective sleeve around the mandrel to be axially displaceable in the device and to have a length such that the shoulder on the rear end of the mandrel is in contact with this tissue protective sleeve when the spiral blade is introduced into the bone.

The spiral blade is typically inserted with the help of a guide wire which is positioned through a drill bush. The drill bush is inserted coaxially through a groove protective sleeve inserted coaxially into the guide sleeve. The cam groove protective sleeve is inserted into the guide sleeve so that the grooves are not damaged during drilling. The length of the spiral blade is then read on the guide wire and the drill bush is removed. Then the lateral cortex is drilled with a drill which is guided axially by the guide wire with the help of the groove protective sleeve and the tissue protective sleeve. Drilling is continued until the drill reaches the stop provided for this purpose on the groove protective sleeve. The groove protective sleeve is then removed, the position is read by the mark on the tissue protective sleeve, and this position is set as the stop by using the limiting element on the mandrel introducing the spiral blade. The mandrel with the spiral blade attached to it is driven in until the limiting element attached to the mandrel as a stop comes in contact with the guide sleeve, and thus the spiral blade is completely inserted.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF PREFERRED EMBODIMENTS

Figure 1:
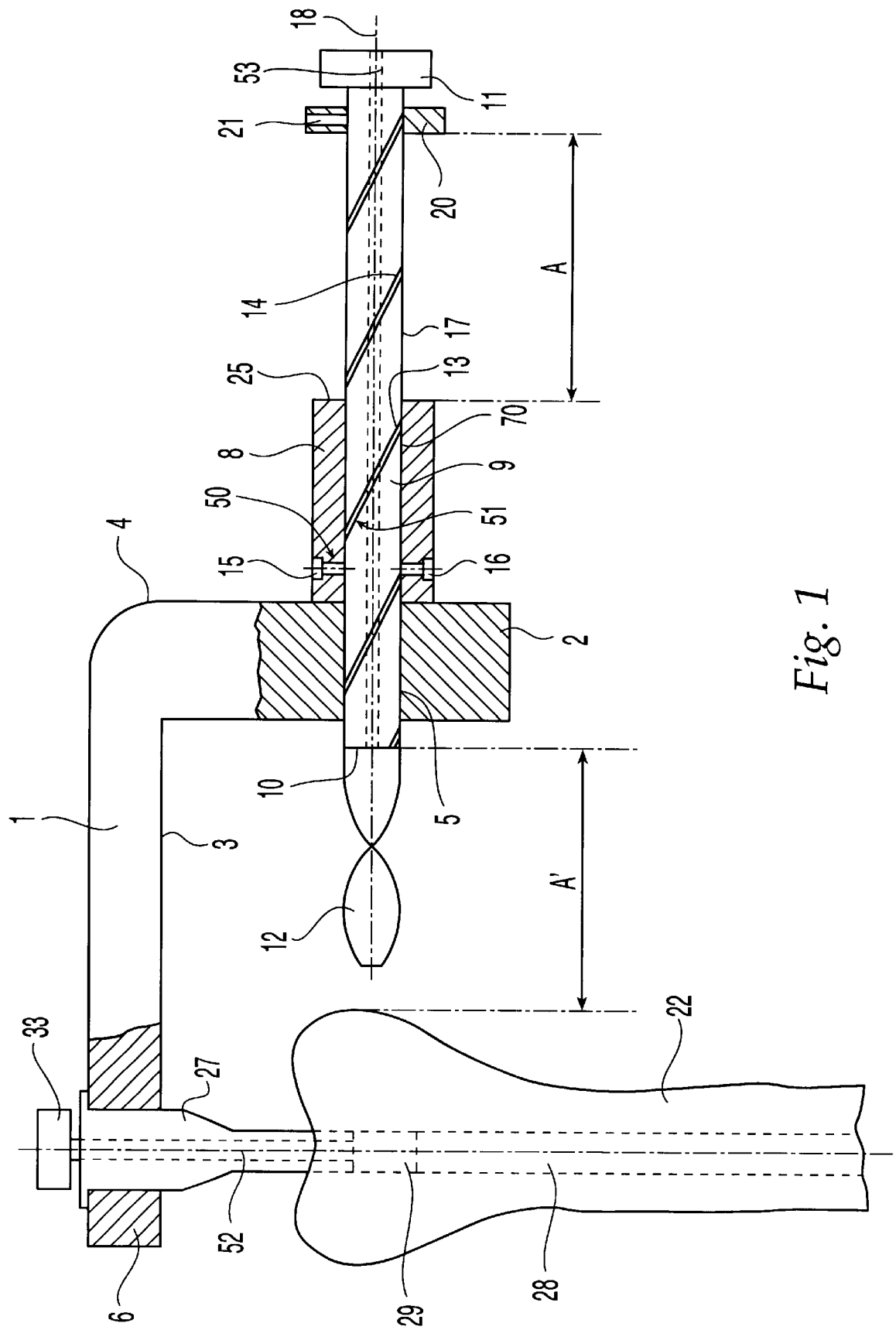
FIG. 1 is a side view of one embodiment of the insertion instrument according to the present invention in use with an intramedullary nail implanted in a bone and a portion of the device shown in cross section.

FIG. 1 shows one embodiment of the device according to the present invention. The device comprises a targeting strap 1 with a through hole 5 on one end 2 of targeting strap 1 extending from an inner surface 3 to an outer surface 4 of targeting strap 1, a guide sleeve 8 secured coaxially with hole 5 and having its own hole 70 with a central axis 18 perpendicular to intramedullary nail 28, and a mandrel 9 that can slide in guide sleeve 8. Targeting strap 1 is configured and dimensioned so that as mandrel 9 is slid into guide sleeve 8, mandrel 9 aligns with a borehole 29 in intramedullary nail 28 into which a spiral blade 12 is introduced. Spiral blade 12 is removably attached to a front end 10 of mandrel 9 so that the rotational orientation of spiral blade 12 with respect to borehole 29 is defined.

Targeting strap 1 is an L-shaped part with a distal end 6 and a proximal end 2. A hole in distal end 6 accommodates a targeting strap tube 27 for coupling with intramedullary nail 28. A connecting screw 33 is inserted in targeting strap tube 27 for connecting targeting strap 1 to intramedullary nail 28 in such a way that targeting strap tube 27 is aligned with the axis of intramedullary nail 28. As a result, the distance between spiral blade 12 and intramedullary nail 28 at the start of the guided movement of mandrel 9 is fixed.

Mandrel 9 is provided with two spiral grooves 13, 14 on its lateral surface 17. Two or more pins 15, 16 are provided in guide sleeve 8 so that they cross central axis 18. Pins 15, 16 are arranged so they are mutually offset and project into hole 70 in guide sleeve 8 so that each of pins 15, 16 engages one of spiral grooves 13, 14. Thus, movement of mandrel 9 into guide sleeve 8 results in helical motion of mandrel 9. As the pitch of each of spiral grooves 13, 14 matches the pitch of spiral blade 12, spiral blade 12 also executes a 360° rotation about its axis when mandrel 9 is rotated 360°. Thus, the position of spiral blade 12 is determined by pins 15, 16 and by spiral grooves 13, 14 on mandrel 9. As there is a correlation between the distance between spiral blade 12 and intramedullary nail 28 and the rotational position of spiral blade 12 (which is defined by guide sleeve 8 and mandrel 9 sliding in it), the cross section of spiral blade 12 fits into borehole 29 when spiral blade 12 comes in contact with intramedullary nail 28.

A limiting element 20 is located on mandrel 9 and secured thereto at any axial location by a locking screw 21. Limiting element 20 limits the axial movement of mandrel 9 through guide sleeve 8 to the distance (A) between limiting element 20 and proximal end of guide sleeve 8. Limiting element 20 can be located on mandrel 9 so that the distance (A) corresponds to the distance (A') traversed by spiral blade 12, i.e. the distance between the end of mandrel 9 and the bone. When introducing spiral blade 12 into bone 22, mandrel 9 can be moved against bone 22 only so far that spiral blade 12 is inserted into bone 22 and into intramedullary nail 28 and distal end 10 of mandrel 9 is in contact with the outside surface of bone 22. Mandrel 9 is also provided with a channel 53 for receiving a guide wire to facilitate implantation of spiral blade 12.

Figure 2:
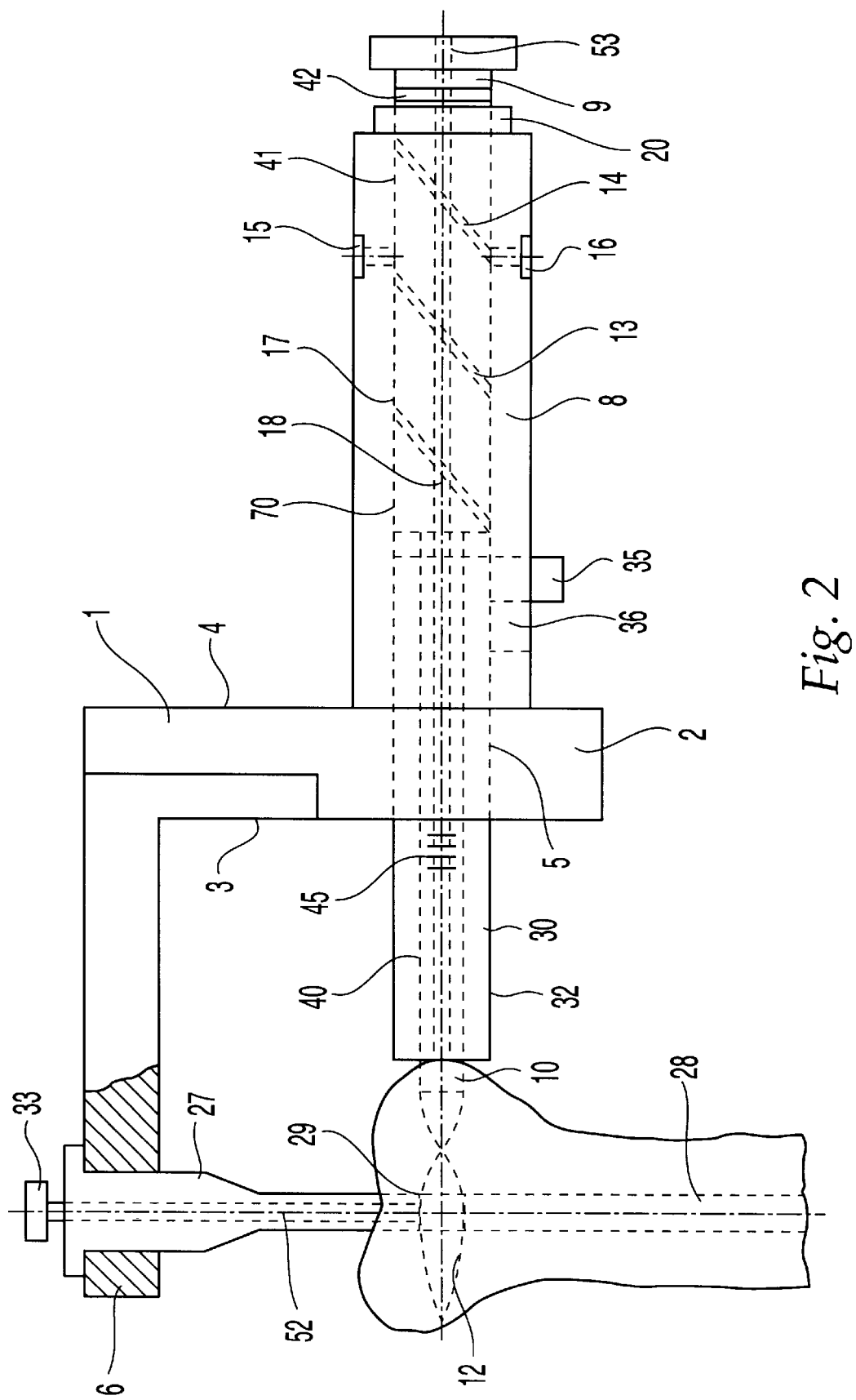
FIG. 2 is a side view of another embodiment of the insertion instrument according to the present invention in use with an intramedullary nail implanted in a bone and a portion of the device shown in cross section.

FIG. 2 shows another embodiment of the device according to the present invention. The device is provided with a tissue protective sleeve 30 to protect the tissue when introducing spiral blade 12. Tissue protective sleeve 30 is mounted so it can slide coaxially with central axis 18 in guide sleeve 8 and it is secured against rotation about the central axis 18 by a handle 35 which is guided in a slot 36 running along central axis 18 in guide sleeve 8. With the help of handle 35, tissue protective sleeve 30 can be removed from guide sleeve 8, the length can be adjusted, and the tissue protective sleeve 30 is secured so that it cannot slip out of targeting strap 1. A lateral surface 32 of tissue protective sleeve 30 is provided with indicia 45 for positioning of tissue protective sleeve 30 lengthwise in the direction of central axis 18.

As shown in FIG. 2, mandrel 9 has a graduated diameter. The diameter of a proximal portion 40 of mandrel 9 is such that it can slide coaxially in tissue protective sleeve 30. A distal portion 41 of mandrel 9 has a larger diameter which fits into hole 70 in guide sleeve 8. Spiral grooves 13, 14 are provided on distal portion 41 of mandrel 9. Accordingly, pins 15, 16 are inserted into guide sleeve 8 at a greater distance from intramedullary nail 28 compared to the embodiment of FIG. 1. This permits a telescoping arrangement of guide sleeve 8 and tissue protective sleeve 30. Then only tissue protective sleeve 30 can be displaced in guide sleeve 8. Guide sleeve 8 is a fixed distance from intramedullary nail 28. Grooves 42 cooperate with limiting element 20 to ensure the maximum depth of penetration of spiral blade 12 by adjusting the amount mandrel 9 can slide into guide sleeve 8.

Figure 3:
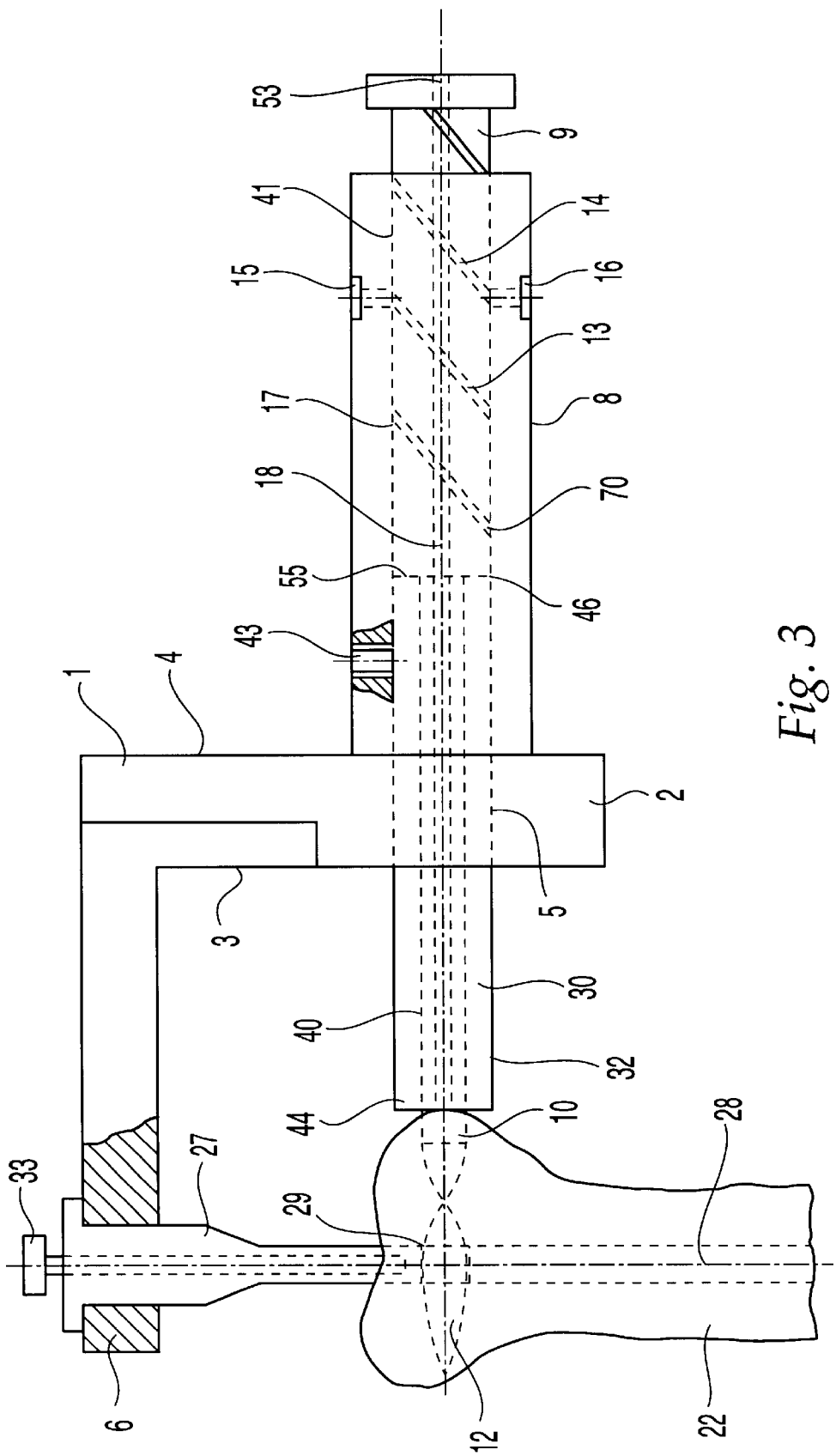
FIG. 3 is a side view of another embodiment of the insertion instrument according to the present invention in use with an intramedullary nail implanted in a bone and a portion of the device shown in cross section.

FIG. 3 shows an embodiment of the device according to the present invention in which tissue protective sleeve 30 also serves as a stop for mandrel 9 on insertion of spiral blade 12. To this end, tissue protective sleeve 30 is in contact with bone 22 before installation of spiral blade 12 and it is blocked in the axial direction by a locking screw 43. The distal portion of mandrel 9 running in guide sleeve 8 has a smaller diameter than its distal portion 41 running in guide sleeve 8. When distal part 41 of mandrel 9 with its larger diameter reaches tissue protective sleeve 30, mandrel 9 is in contact with tissue protective sleeve 30, and therefore cannot be brought further in the direction of bone 22. As described with respect to the other embodiments, distal portion 41 of mandrel 9 can be provided with spiral grooves 13, 14 on its lateral surface 17 and guide sleeve 8 can be provided with pins 15, 16 to achieve helical motion of mandrel 9 (and spiral blade 12). Alternatively, a single-lead or multiple lead thread can be provided on mandrel 9 and in guide sleeve 8 to result in the helical motion. Shoulder 55 of mandrel 9 may contact proximal end 46 of tissue protective sleeve 30.

Figure 4:
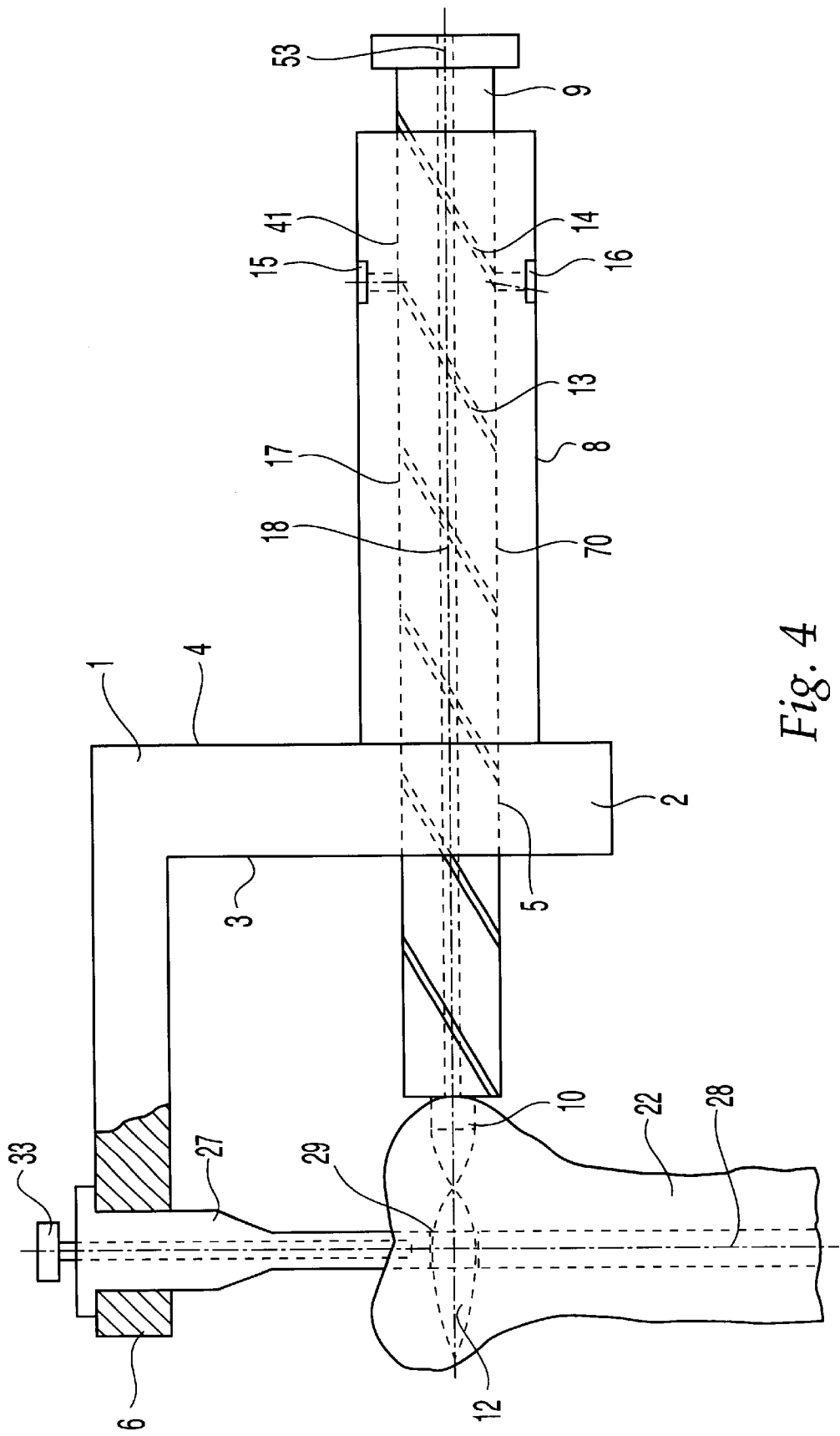
FIG. 4 is a side view of another embodiment of the insertion instrument according to the present invention in use with an intramedullary nail implanted in a bone and a portion of the device shown in cross section.

FIG. 4 shows an embodiment in which the diameter of mandrel 9 is larger than that of spiral blade 12. Therefore, when spiral blade 12 is inserted, mandrel 9 is in contact with the surface of bone 22 and thus it is not necessary to have a stop in the axial direction. The helical motion of mandrel 9 and spiral blade 12 can be achieved with either the spiral groove/pin arrange or the single-lead/multiple lead thread arrangement.

Figure 5:
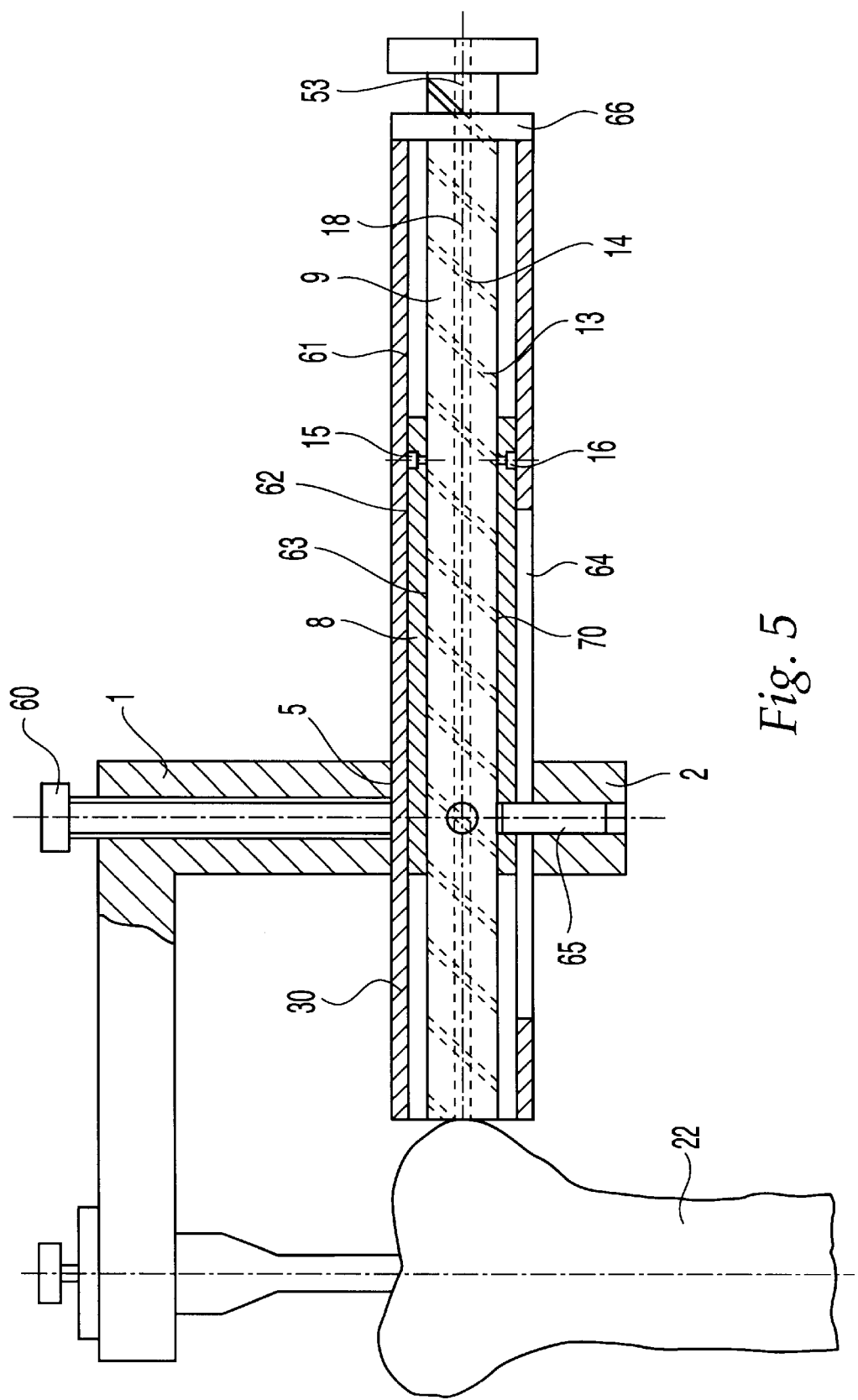
FIG. 5 is a side view of another embodiment of the insertion instrument according to the present invention having a tissue protective sleeve and in use with an intramedullary nail implanted in a bone and a portion of the device shown in cross section.

FIG. 5 shows an embodiment similar to that of FIG. 3 in which the device is axially secured in tissue protective sleeve 30 with respect to targeting strap 1. Tissue protective sleeve 30 can slide in hole 5 in targeting strap 1 and is displaceable in the direction of central axis 18 in both directions. Once tissue protective sleeve 30 has been brought to the correct position axially, it can be secured in targeting strap 1 by means of a locking screw 60 running in targeting strap 1. The length of tissue protective sleeve 30 is such that a fixed stop 66 mounted on mandrel 9 is in contact with the end of tissue protective sleeve 30 remote from bone 22 when spiral blade 12 has been introduced into intramedullary nail 28 as illustrated in FIG. 2. Guide sleeve 8 is provided concentrically with central axis 18 in hole 61 in tissue protective sleeve 30 and is secured in the axial direction by pins 65 which are anchored in guide sleeve 8 and in the targeting strap 1. To prevent tissue protective sleeve 30 from being displaced in the direction of central axis 18, it is provided with elongated holes 64 which serve as recesses for pins 65 securing guide sleeve 8. Thus, tissue protective sleeve 30, as well as mandrel 9, can be moved in the direction of central axis 18 without guide sleeve 8 being moved axially. As a result, the position of pins 15, 16 with respect to targeting strap 1 is also fixed. In other words, the position of spiral blade 12 can also be secured by pins 15, 16 and spiral grooves 13, 14 in any axial position of mandrel 9. As previously described, a single-lead or multiple lead thread may also be provided on mandrel 9 and in guide sleeve 8 instead of spiral grooves 13, 14 on mandrel 9 and pins 15, 16 in guide sleeve 8.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An insertion instrument for inserting a spiral blade through a borehole in an implanted intramedullary nail having a longitudinal axis, the instrument comprising:

a targeting strap having first and second arms, the first arm having a through hole;

a guide sleeve operatively associated with the targeting strap and having a central axis, an opening running coaxially with the through hole, and a first engaging element; and a mandrel slideably receivable in the opening and having proximal and distal ends and a second engaging element, wherein the first and second engaging elements cooperate to convert an axial force on the mandrel to helical motion of the mandrel such that a spiral blade detachably mounted to the distal end of the mandrel is properly oriented to be received by the borehole.

2. The insertion instrument of claim 1 further comprising a hole in the second arm, a targeting strap tube insertable in the hole and a connecting member insertable in the targeting strap tube for positioning and securing the targeting strap to the intramedullary nail.

3. The insertion instrument of claim 2 wherein the first and second engaging elements are positioned with respect to each other so that the mandrel intersects an axis of the targeting strap tube, said axis intersecting the central axis and running at an angle to the central axis.

4. The insertion instrument of claim 1 wherein the first engaging element is a pin extending across the central axis of the guide sleeve and the second engaging element is a spiral groove on the mandrel, the pin engaging the spiral groove to allow helical motion of the mandrel.

5. The insertion instrument of claim 4 wherein the second engaging element comprises first and second spiral grooves mutually offset by about 180 degrees on a lateral surface of the mandrel.

6. The insertion device of claim 5 wherein the spiral blade has a pitch and the first and second spiral grooves pitch matches the pitch of the spiral blade.

7. The insertion device of claim 6 wherein the first engaging element includes first and second pins extending across the central axis of the guide sleeve and configured and dimensioned so that each of the first and second pins engages one of the first and second spiral grooves.

8. The insertion device of claim 1 wherein the first engaging element is a thread on a lateral surface of the mandrel and the second engaging element is a mating thread on the opening in the guide sleeve.

9. The insertion device of claim 1 wherein the guide sleeve is attached to the first arm of the targeting strap.

10. The insertion device of claim 1 further comprising a tissue protective sleeve for protecting tissue near a bone and having a bore running coaxially with the central axis.

11. The insertion device of claim 10 wherein at least a portion of the tissue protective sleeve is slidably received in the opening of the guide sleeve.

12. The insertion device of claim 11 wherein the tissue protective sleeve has a handle and the guide sleeve has a slot with the handle moveable within the slot to slide the tissue protective sleeve in the opening of the guide sleeve and prevent rotation of the tissue protective sleeve.

13. The insertion device of claim 11 wherein a lateral surface of the tissue protective sleeve is provided with indicia for selectable axial positioning.

14. The insertion device of claim 11 wherein the mandrel has a shoulder that contacts a proximal end of the tissue protective sleeve when a spiral blade is received in the borehole.

15. The insertion device of claim 1 wherein the proximal end of the mandrel has a head that has a diameter larger than that of the opening.

16. The insertion device of 15 wherein the head of the mandrel contacts a proximal end of the guide sleeve when the spiral blade is received in the borehole.

17. The insertion device of claim 1 further comprising a limiting element securable on the mandrel for limiting the amount of movement of the mandrel into the opening.

18. The insertion device of claim 17 wherein the limiting element is securable on the mandrel in any one of a plurality of positions.

19. An insertion instrument for inserting a spiral blade through a borehole in an implanted intramedullary nail having a longitudinal axis, the instrument comprising:

a targeting strap having first and second arms, the first arm having a through hole; disposed along a first axis;

an alignment element associated with the through hole and including a locking element disposed transverse to the first axis; and a spiral blade wherein the spiral blade is received in the alignment element to align the blade with the borehole in the nail.

20. The insertion instrument of claim 19 wherein the locking element comprises a pin.

* * * * *